United States Patent [19]

Miller et al.

[11] Patent Number: 4,874,732

[45] Date of Patent: Oct. 17, 1989

[54] COBALT FISCHER-TROPSCH CATALYSTS HAVING IMPROVED SELECTIVITY

[75] Inventors: James G. Miller, Pearl River; Jule A. Rabo, Armonk, both of N.Y.

[73] Assignee: UOP, Des Plaines, Ill.

[21] Appl. No.: 72,747

[22] Filed: Jul. 13, 1987

[51] Int. Cl.$^4$ .............................................. B01J 29/10
[52] U.S. Cl. ........................................ 502/74; 502/66
[58] Field of Search ...................... 502/66, 74; 518/715

[56] References Cited

U.S. PATENT DOCUMENTS

| | | | |
|---|---|---|---|
| 2,244,196 | 6/1941 | Herbert | 518/715 |
| 2,248,734 | 7/1941 | Barr | 518/715 |
| 4,207,208 | 6/1980 | Lucki et al. | 502/66 |
| 4,207,248 | 6/1980 | Butter et al. | 502/66 |
| 4,207,250 | 6/1980 | Butter et al. | 502/66 |
| 4,640,766 | 2/1987 | Post et al. | 518/715 |
| 4,652,538 | 3/1987 | Rabo et al. | 502/66 |
| 4,670,472 | 6/1987 | Dyer et al. | 518/715 |

FOREIGN PATENT DOCUMENTS

| | | | |
|---|---|---|---|
| 44740 | 1/1982 | European Pat. Off. | 518/715 |
| 192834 | 11/1983 | Japan | 502/74 |
| 150102 | 9/1962 | U.S.S.R. | |

OTHER PUBLICATIONS

Anderson, Robert B., The Fischer-Tropsch Synthesis, Academic Press, Orlando, Fla., 1984, pp. 123–129.
Dent, A. L. and Lin, M., Adv. Chem. Ser., 178, pp. 47–63.
Eidus, Ya. T. et al., Scientific Selection of Catalysts, Daniel Davey & Company, Jerusalem, 1968, pp. 206–213.

*Primary Examiner*—Carl F. Dees
*Attorney, Agent, or Firm*—Thomas K. McBride

[57] ABSTRACT

The promoter(s) Mn oxide or Mn oxide and Zr oxide are added to a cobalt Fischer-Tropsch catalyst combined with the molecular sieve TC-103 or TC-123 such that the resultant catalyst demonstrates improved product selectivity, stability and catalyst life. The improved selectivity is evidenced by lower methane production, higher C5+ yield and increased olefin production.

5 Claims, No Drawings

COBALT FISCHER-TROPSCH CATALYSTS HAVING IMPROVED SELECTIVITY

STATEMENT

The Government of the United States of America has rights to this invention pursuant to Contract No. DE-AC22-84PC70028 awarded by the U.S. Department of Energy.

FIELD OF THE INVENTION

The present application relates to the field of cobalt Fischer-Tropsch catalysts in combination with various molecular sieves which have been further promoted to improve product selectivity and stability.

BACKGROUND OF THE INVENTION

Iron Fischer-Tropsch (F-T) catalysts have generally been preferred commercially over cobalt based catalysts and are presently the only commercial F-T catalyst used.

While cobalt catalysts have the benefit of higher activity and better selectivity to motor fuels they suffer from their inherent production of excess methane (an undesirable product) as well as the paraffinic nature of the product. It would be an important catalyst improvement if a stable cobalt F-T catalyst was discovered which demonstrated reduced methane production, increased C5+ yield and improved olefin content, especially in the C5− range.

Prior art teaching for the use of promoted cobalt oxide in the Fischer Tropsch process has been well established, including the commercial use of a thorium, magnesium promoted cobalt kieselguhr catalyst in Germany in the 1930's and 40's. A large number of literature studies have been published and patents issued in the area, many dealing with the use of various promoters to improve catalyst performance.

An excellent review of past publications on cobalt Fischer-Tropsch catalyst was reported by R. B. Anderson, "The Fischer-Tropsch Synthesis", Academic Press, Orlando FL, 1984. In the review are lists of promoters and catalysts studied in the past, included are sightings of the use of Mn and Zr promoters. Listed below is a summary of the information presented in this article related to the use of the Mn and Zr promoters. Fischer and Koch showed Mn added to a cobalt kieselguhr catalyst was effective at shifting the product distribution toward heavier product as was also observed for the catalysts in this invention. Work by Eidus and Bulanova showed a similar effect on the addition of $ZrO_2$ to the same type of catalyst, this was not observed upon our addition of $ZrO_2$ to the Mn promoted Co/TC-123 catalyst system. No work to our knowledge has been reported on the use of a combined Mn and Zr promoted catalyst Dent, A. L. and Lin, M., Adv. Chem. Ser. 178,47 (1979) reported that the addition of Mn to a cobalt alumina catalyst increased the olefin content in the product, which is consistent with our data.

The only prior art of which the applicants are aware relating Zr for improving the stability of a cobalt F-T catalyst was reported by Eidus and Bulanova U.S.S.R. 150,102, Sept. 26, 1962, Appl. Nov. 27, 1954. In this work Zr was used in place of thorium to reduce the sensitivity of the catalyst to super heating. The applicants are not aware of any prior art which teaches the use of Mn to improve cobalt catalyst stability.

SUMMARY OF THE INVENTION

The present invention is directed to a cobalt Fischer-Tropsch Catalyst/Molecular Sieve combination which has been modified using a promoter selected from the group comprising Mn oxide or the combination of Mn oxide and Zr oxide.

It has been found that the resulted catalyst demonstrates superior product selectivity and stability which is evidenced by lower methane production, higher C5+ yields, increased olefin production, and longer catalyst life.

DESCRIPTION OF THE INVENTION

We have found that when the promoter(s) Mn oxide or the combination of Mn oxide and Zr oxide are added to a cobalt F-T catalyst supported on the molecular sieves TC-103 or TC-123 that the catalyst s performance is significantly improved. The use of a cobalt catalyst in combination with TC-103 (acid extracted LZ-10) was previously reported by Rabo et al. - U.S. Pat. No. 4,652,538, where TC- 103 represents an acid extracted ultrahydrophobic Y molecular sieve. The use of the molecular sieve TC-123 is disclosed by Miller et al (U.S. patent application Ser. No. 72,748, filed concurrently herewith) where TC-123 represents a steam treated, acid extracted LZ-210. Addition of Mn oxide was found to significantly reduce methane production. This decrease resulted from shifting of the product slate toward heavier, more desirable product. A significant increase in product yield above the motor fuels range was observed, but this could easily be hydroprocessed back into the motor fuel boiling point range. The Mn oxide promoter acts to reduce the hydrogenation ability of the cobalt catalyst, promoting hydrocarbon chain growth over chain termination. Consistent with this theory the olefin content of the F-T product is increased in the presence of the MN additive.

Surprisingly, in spite of the reduced hydrogenation activity, the addition of the Mn promoter was also found to greatly increase the cobalt catalyst's stability. A ten fold decrease in the deactivation rate was observed upon addition of Mn to a cobalt TC-123 catalyst. Comparison of a Mn promoted γ-alumina catalyst to that of a TC-103 catalyst showed that a synergistic stabilizing effect existed between the Mn promoter and the molecular sieve chosen, not observed for a typical catalyst support like γ-alumina. Further stabilization of the molecular sieve supported Mn promoted cobalt catalyst was found by the addition of Zr oxide, without significantly effecting the product selectivity.

Characterization of the cobalt molecular sieve catalysts shows the promoted cobalt being encapsulated within the secondary pore structure of the molecular sieve support. The secondary pores in the molecular sieve crystal aid in tailoring and maintaining the cobalt particles at the optimum size for maximum activity and selectivity while allowing the syngas and products to diffuse through the primary zeolite pore structure. The promoters further prevent the cobalt metal particle from sintering and moving to the outside of the molecular sieve crystals.

EXAMPLES

While the invention has been described above the details of the present invention will be better understood by recourse of the following examples which serve to illustrate the following:

The addition of Mn oxide to a cobalt TC-123 catalyst significantly improves the catalyst's stability, product selectivity and activity.

The addition of Mn oxide to a cobalt/TC-103 catalyst significantly improves the catalyst's stability and product selectivity.

The addition of Zr oxide to a Mn promoted Co/TC-123 catalyst further increased catalyst stability while having little effect on product selectivity.

The Mn promoted cobalt TC-103 catalyst has superior stability to a Mn promoted cobalt supported on a conventional support like γ-alumina.

EXAMPLE I

The following example compares a manganese oxide promoted and a non-promoted cobalt/TC-123 F-T catalyst. The Mn promoter was found to significantly improve the activity, product selectivity and stability of the cobalt/TC-123 catalyst.

The catalysts were both prepared by the same procedure. Typically the molecular sieve TC-123 (100q anhydrous) was pore filled with an ethylene glycol solution containing 55.8 g Co(NO3) 6H20, 7.21 Mn(NO3)2 xH2O and 48.0 g ethylene glycol. The TC-123 molecular sieve support was prepared by treating steam stabilized, ammonium exchanged LZ-210 with a SiO$_2$/Al$_2$O$_3$ ratio of 9.0 with 1 atmosphere of steam at 750° C. for 1 hour, followed by acid extraction in 3M HCl under reflux conditions for 3 hours. The support was filtered, water washed and dried at 11° C. overnight. Prior to pore filling the ethylene glycol solution was heated to 50° C. for 1 hour. The powder was dried using the following procedure: 110° C. for 10 hours, 200° C. for 30 minutes, and 450° C. for 4 hours. The catalyst was then bonded with 15% silica (Nalco), extruded into ⅛" extrudates, dried at 110° C. and calcined at 250° C. for 2 hours. The calculated percent of cobalt and manganese in the catalysts based on raw materials used were 8.3% Co, 0.0% Mn, and 8.2% Co, 1.6% Mn.

Catalyst samples were loaded into a Berty type internal recycling reactor and hydrogen treated at 350C, 300 psig for 18 hours and exposed to 1:1 H2:CO syngas at 220° C. The catalysts were tested at 240° C., 300 psig, 300 GHSV, 1:1 H2:CO as well as 260° C., 500 psig, 300 GHSV, 1.5:1 H2:CO.

Results of the testing are illustrated in Table 1 and 2. The Mn oxide promoted catalyst performed significantly better than the non-promoted catalyst under both the 240° C. and 260° C. conditions. The syngas conversion activity of the cobalt catalyst was improved by more than 10%. Furthermore, selectivity of the promoted catalyst showed a desirable decrease in methane production, about ½ that of the non-promoted catalyst. In addition, a significant increase in C5+ yield was also observed. The majority of the C5+ yield increase was observed in the 650F+wax fraction which is easily hydroprocessed into the motor fuels range. Hydrogen economy and product quality was also improved by the increase of olefin content of the product, evidenced by the increase in the olefin/paraffin ratio of the C4 product.

In addition to the benefits cited above a major benefit of the Mn oxide promoter was it's effect on catalyst stability. The catalyst showed a ten fold decrease in the percent syngas conversion loss per hour than the non-promoted catalyst under the 260° C. conditions. The deactivation rate was based on a least squares analysis. Such reduced deactivation rate implies a several fold increase in catalyst life. Since catalyst cost is an important component of F-T product cost, such a large increase in catalyst life provides important economic benefit for the Mn promoted catalyst.

TABLE 1

Comparison of Co/TC-123 and Mn Oxide Promoted Co/TC-123 Fischer-Tropsch Catalyst

| Catalyst: | Co/TC-123 | | Co/Mn/Tc-123 | |
|---|---|---|---|---|
| Temperature | 240° C. | 260° C. | 240° C. | 260° C. |
| H2:CO | 1:1 | 1.5:1 | 1:1 | 1.5:1 |
| Pressure | 300 | 500 | 300 | 500 |
| Conversion | 42 | 73 | 48 | 81 |
| CH4 | 6.7 | 26.0 | 3.3 | 12.2 |
| C2–C4 | 9.2 | 14.3 | 7.8 | 10.4 |
| C5–350° F. | 25.0 | 26.2 | 21.4 | 29.6 |
| 350–650° F. | 35.1 | 22.3 | 29.0 | 30.1 |
| 650° F.+ | 24.6 | 11.2 | 38.6 | 17.7 |
| C5+ | 84.8 | 59.7 | 88.9 | 77.4 |
| C4 ole./par. | 1.8 | .5 | 3.7 | .9 |
| Stability(a) | — | .2 | — | .02 |

Space velocity - 300 GHSV
(a)Percent loss in syngas conversion per hour.

EXAMPLE II

The following example compares a manganese oxide promoted cobalt oxide catalyst and a non-promoted cobalt oxide catalyst both supported on TC-103 (acid extracted LZ-10). Similar to Example I, the Mn promoter was found to improve catalyst performance by increasing catalyst stability and improving product selectivity.

The two catalysts were prepared under almost identical conditions. The non-promoted catalyst utilized the procedure described for the catalysts in Example I. The Mn promoted catalyst was prepared by a similar method, however the drying and calcining procedure (ramping to 450° C.) was not performed and the pore filled material was dried at 110° C. overnight. The calcining procedure change should have little effect on the overall catalyst performance. The calculated percent cobalt and manganese in the catalysts based on raw material used were 12.8% Co, 0.0% Mn and 12.3% Co, 2.4% Mn. Fischer-Tropsch testing was performed as described in Example I. The non-promoted catalyst was exposed to 1:1 H2:CO and 260° C. initially and the Mn promoted catalyst was exposed to 1:1 H2:CO initially at 220° C.

Results of the testing are illustrated in Table 2.

Similar to the TC-123 system (Example I) the Mn oxide promoter served to decrease methane production, increase C5+yield and increase the olefin to paraffin ratio of the product. Unlike the TC-123 system the promoted catalyst showed lower syngas conversion activity however it demonstrated superior stability both in syngas conversion and in product selectivity. The syngas conversion of the non-promoted catalyst showed a rapid drop, about 9% conversion in 94.5 hours compared to only 1.8% over 144 hours for the promoted catalyst. Thus, under practical conditions over desired catalyst life times of greater than 6 months the Mn promoted catalyst is expected to show much superior overall activity relative to the non-promoted catalyst.

TABLE 2

Comparison of Co/TC-103 and Mn Oxide Promoted Co/TC-103 Fischer-Tropsch Catalysts

| Catalyst: | Co/TC-103 | | Co/Mn/TC-103 | |
|---|---|---|---|---|
| TOS | 71.1 | 165.5 | 167.5 | 311.5 |
| H2:CO | 1:1 | 1:1 | 1:1 | 1:1 |
| Pressure | 300 | 300 | 300 | 300 |
| Conversion | 77.8 | 68.5 | 54.0 | 52.2 |
| CH4 | 10.1 | 16.1 | 6.5 | 6.3 |
| C2–C4 | 9.6 | 10.9 | 10.7 | 11.1 |
| C5–420° F. | 39.4 | 39.9 | 34.4 | 36.0 |
| 420–700° F. | 31.0 | 25.1 | 28.5 | 29.4 |
| 700° F.+ | 9.9 | 8.1 | 19.9 | 17.3 |
| C5+ | 80.3 | 73.1 | 82.8 | 82.6 |
| C4 ole./par. | 1.6 | .9 | 2.2 | 2.2 |

Space velocity = 300 GHSV, Temperature = 260° C.

EXAMPLE III

The following example compares a Mn oxide promoted Co/TC-123 catalyst to one promoted by both Mn oxide and Zr oxide. The added zirconium oxide promoter greatly increased catalyst stability while having only minor affects on the catalyst's activity and selectivity.

The catalysts were prepared as described in Example I except in the Mn and Zr promoted catalysts ZrO(NO3)2 (5.62 g) was added to the ethylene glycol solution used to pore fill the TC-123 molecular sieve. The calculated percentage of cobalt, manganese, and zirconium in the catalysts based on raw materials used were 8.2% Co, 1.6% Mn, 0.0% Zr and 8.2% Co, 1.6% Mn, 1.1% Zr. Fischer-Tropsch testing was as described in Example 1.

The results of F-T testing are illustrated below in Table 3.

Under the conditions tested the Zr oxide promoted catalyst was found to reduce syngas conversion only to a small extent while it had almost no effect on the product selectivity. Importantly, it decreased the rate of deactivation of syngas conversion by a factor of three over the Mn promoted catalyst. Stability was based on a linear least square estimate of the percent loss in syngas conversion per hour. The increase in catalyst stability observed for the combined Mn and Zr promoted catalyst would further increase both catalyst life and the economic benefit of the Mn only promoted catalyst described in Example I. Product quality was only slightly changed, showing a partial loss of the increased olefin content in the product caused by the Mn oxide promoter.

TABLE 3

Comparison of Mn and Mn/Zr Oxide Promoted Co TC-123 Fischer-Tropsch Catalysts

| Catalyst: | Co/Mn/Zr/TC-123 | | CO/Mn/TC-123 | |
|---|---|---|---|---|
| Temperature | 240° C. | 260° C. | 240° C. | 260° C. |
| H2:CO | 1:1 | 1.5:1 | 1:1 | 1.5:1 |
| Pressure | 300 | 500 | 300 | 500 |
| Conversion | 41 | 77 | 48 | 81 |
| CH4 | 3.5 | 10.0 | 3.3 | 12.2 |
| C2–C4 | 7.7 | 11.0 | 7.8 | 10.4 |
| C5–350° F. | 21.4 | 29.0 | 21.4 | 29.6 |
| 350–650° F. | 29.7 | 27.9 | 29.0 | 30.1 |
| 650° F.+ | 37.7 | 22.0 | 38.6 | 17.7 |
| C5+ | 88.8 | 79.0 | 88.9 | 77.4 |
| C4 ole./par. | 2.6 | 1.0 | 3.7 | .9 |
| Stability[a] | — | .007 | — | .02 |

Space velocity = 300 GHSV
[a]Percent loss in syngas conversion per hour.

EXAMPLE IV

The following example compares a TC-103 and a γ-alumina supported cobalt Fischer-Tropsch catalyst promoted with manganese oxide. The TC-103 supported catalyst showed superior product selectivity over the γ-alumina catalyst and in addition demonstrated much superior stability.

The two catalysts were prepared under identical conditions using the method described for the catalysts in Example II. In the alumina supported case Kaiser γ-alumina was substituted for the molecular sieve support. The calculated percent cobalt and manganese in the catalyst, based on the raw materials used, was in both cases 8.2% Co and 1.6% Mn. Fischer-Tropsch testing was as described in Example I, with both catalysts exposed to 220° C., 300 psig, 1:1 H2:CO syngas, and 300 GHSV after hydrogen treatment.

Results of testing are illustrated in Table 4 below.

The major advantage of using TC-103 as the support was shown in C5+ product selectivity and particularly in stability of the catalyst under the conditions tested. The γ-alumina catalyst showed a 0.03% syngas conversion loss per hour compared to the TC-103 catalyst which showed essentially no deactivation over the period tested. The rate of deactivation was based on a linear least squares analysis of the loss in syngas conversion over the length of the test. The analysis included all except the first data point for each catalyst, Table 4 shows only the first and last data point used for the analysis.

The activity and selectivity of the two catalysts were fairly similar with the γ-alumina catalyst showing slightly higher initial activity. However, under practical conditions and realistic expected catalyst life times the activity of the γ-Al2O3 supported catalyst would be grossly inferior relative to the TC-103 supported catalyst. In addition, the TC-103 catalyst showed slightly better product selectivity: reduced methane, higher C5+.

TABLE 4

Comparison of Mn Oxide Promoted γ-Alumina and TC-103 Cobalt Fischer-Tropsch Catalysts

| Catalyst: | Co/Mn | γ-Al2O3 | Co/Mn/TC-103 | |
|---|---|---|---|---|
| HOS | 186 | 258 | 338 | 403 |
| HOS at 260° C. | 48 | 120 | 48 | 168 |
| Conversion | 60.7 | 58.2 | 58.1 | 57.6 |
| CH4 | 8.8 | 10.0 | 7.6 | 8.6 |
| C2–C4 | 12.1 | 13.6 | 10.3 | 10.6 |
| C5–420° F. | 42.2 | 39.0 | 36.6 | 36.7 |
| 420–700° F. | 26.8 | 29.1 | 26.8 | 27.2 |
| 700° F.+ | 10.1 | 8.3 | 18.7 | 16.9 |
| C5+ | 79.1 | 76.5 | 82.1 | 80.8 |
| C4 ole./par. | 2.0 | 1.9 | 1.8 | 1.7 |
| Stability[a] | .03 | | .001 | |

Conditions: 260° C., 300 psig, 1:1 H2:CO, 300 GHSV HOS = Hours on stream
[a]Percent loss in syngas conversion per hour.

While the invention has been described with respect to various specific examples and embodiments, it is to be understood that the invention is not limited thereto and that it can be variously practiced within the scope of the following claims.

We Claim:

1. A cobalt Fischer Tropsch catalyst supported by an ultrahydrophobic molecular sieve in combination with an effective amount of a promoter selected from the group comprising Mn oxide and the combination of Mn oxide and Zr oxide.

2. A cobalt Fischer-Tropsch catalyst according to claim 1 wherein the promoter is Mn oxide.

3. A cobalt Fischer Tropsch catalyst according to claim 1 wherein the promoter is a combination of Mn oxide and Zr oxide.

4. A cobalt Fischer Tropsch catalyst according to claim 1 wherein the ultrahydrophobic molecular sieve support is a acid extracted LZ-10 molecular sieve.

5. A cobalt Fischer Tropsch catalyst according to claim 1 wherein the ultrahydrophobic molecular sieve support is a steam treated and acid extracted LZ-210 molecular sieve.

* * * * *